(12) United States Patent
Salomon et al.

(10) Patent No.: US 10,620,094 B2
(45) Date of Patent: Apr. 14, 2020

(54) SAMPLING DEVICE FOR WITHDRAWING FLUID SAMPLES FROM A FLUID CONTAINER

(71) Applicant: KEOFITT A/S, Svendborg (DK)

(72) Inventors: Henrik L. Salomon, Svendborg (DK); Henrik Neuschäfer Larsen, Søborg (DK); Allan Otto Kjær, Hvidovre (DK)

(73) Assignee: KEOFITT A/S, Svendborg (DK)

(*) Notice: Subject to any disclaimer, the term of this patent is extended or adjusted under 35 U.S.C. 154(b) by 168 days.

(21) Appl. No.: 15/566,063

(22) PCT Filed: Apr. 12, 2016

(86) PCT No.: PCT/EP2016/057984
§ 371 (c)(1),
(2) Date: Oct. 12, 2017

(87) PCT Pub. No.: WO2016/166089
PCT Pub. Date: Oct. 20, 2016

(65) Prior Publication Data
US 2018/0136092 A1  May 17, 2018

(30) Foreign Application Priority Data
Apr. 14, 2015  (EP) .................................. 15163576

(51) Int. Cl.
*G01N 1/18*  (2006.01)
*F16K 3/08*  (2006.01)
(Continued)

(52) U.S. Cl.
CPC ............... *G01N 1/18* (2013.01); *C12M 33/00* (2013.01); *F16K 3/085* (2013.01); *F16K 11/165* (2013.01);
(Continued)

(58) Field of Classification Search
CPC ......... G01N 1/18; F16K 3/085; F16K 31/535; F16K 1/165
See application file for complete search history.

(56) References Cited

U.S. PATENT DOCUMENTS 3,747,630 A * 7/1973 Hurrell ................. F16K 11/074
137/312
3,868,970 A * 3/1975 Ayers .................... F16K 11/074
137/625.46
(Continued)

FOREIGN PATENT DOCUMENTS

EP      1548420 A2    6/2005
WO   2007143426 A2   12/2007

OTHER PUBLICATIONS

International Search Report, Application No. PCT/EP2016/057984, dated Jun. 14, 2016, 3 pages.
(Continued)

*Primary Examiner* — Brian R Gordon
(74) *Attorney, Agent, or Firm* — Ziegler IP Law Group, LLC

(57) ABSTRACT

A sampling device for withdrawing a plurality of samples from a fluid container. The sampling device includes a support member for mounting into a port of a fluid container and a plurality of rotatable inserts, each insert having a through conduit forming an eccentric aperture within the distal end surface of insert, the through conduit being alignable and misalignable with a respective through passage of the support member by rotating the insert relative to the support member. In another aspect, the present disclosure relates to a method of withdrawing a sample from a fluid container and the use of cylindrical elements to that effect.

19 Claims, 7 Drawing Sheets

Figure 1:
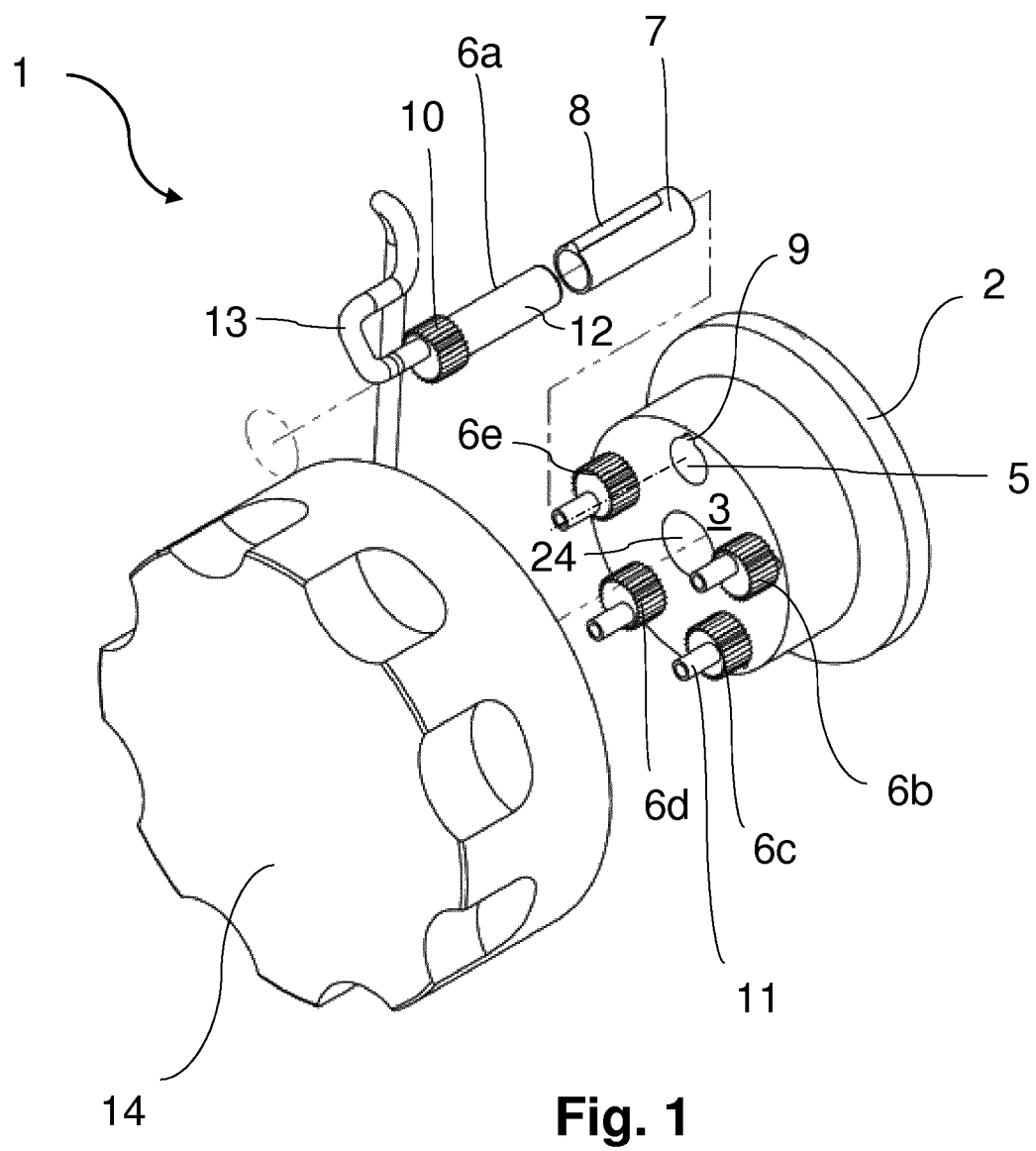

(51) Int. Cl.
  *F16K 31/53*  (2006.01)
  *F16K 11/16*  (2006.01)
  *G01N 1/10*  (2006.01)
  *C12M 1/26*  (2006.01)

(52) U.S. Cl.
  CPC ............ *F16K 31/535* (2013.01); *G01N 1/10* (2013.01); *G01N 2001/1037* (2013.01)

(56) References Cited

U.S. PATENT DOCUMENTS

| | | | | |
|---|---|---|---|---|
| 4,694,861 A * | 9/1987 | Goodale | ................ | F16K 7/045 137/595 |
| 4,702,889 A * | 10/1987 | Cabrera | ................ | G01N 1/38 137/240 |
| 4,705,627 A * | 11/1987 | Miwa | ................ | B01D 15/1842 137/625.46 |
| 4,948,565 A * | 8/1990 | Bemis | ................ | G01N 35/1097 251/355 |
| 5,207,109 A * | 5/1993 | Olsen | ................ | G01N 30/20 73/863.73 |
| 5,250,263 A * | 10/1993 | Manz | ................ | B01J 19/0093 422/504 |
| 5,823,222 A | 10/1998 | Minshull et al. | | |
| 6,322,752 B1 * | 11/2001 | Siddiqui | ................ | G01N 35/10 422/105 |
| 6,447,678 B2 * | 9/2002 | Chau | ................ | C02F 1/003 137/625.46 |
| 6,852,291 B1 * | 2/2005 | Johnson | ................ | B01J 19/0046 137/597 |
| 6,945,264 B1 * | 9/2005 | Denzel | ................ | F16K 3/085 137/1 |
| 8,758,708 B2 * | 6/2014 | Brenneis | ................ | G01N 1/14 141/309 |
| 10,113,995 B2 * | 10/2018 | Hartmann | ................ | G01N 30/20 |
| 10,124,335 B2 * | 11/2018 | Liang | ................ | F16K 99/0013 |
| 2003/0064007 A1 * | 4/2003 | Kim | ................ | G01N 1/16 422/509 |
| 2003/0162304 A1 * | 8/2003 | Dority | ................ | B01L 3/502 436/180 |
| 2005/0277848 A1 * | 12/2005 | Graf | ................ | A61B 10/0096 600/575 |
| 2006/0272432 A1 | 12/2006 | Belongia | | |
| 2007/0204924 A1 | 9/2007 | Delgiacco et al. | | |
| 2007/0278439 A1 | 12/2007 | Martin | | |
| 2008/0022785 A1 | 1/2008 | Furey et al. | | |
| 2009/0019954 A1 | 1/2009 | Evans | | |
| 2011/0006237 A1 * | 1/2011 | Tower | ................ | F16K 3/08 251/304 |
| 2012/0192954 A1 * | 8/2012 | Jorgenson | ................ | F16K 3/085 137/2 |
| 2014/0014231 A1 | 1/2014 | Guedon | | |
| 2014/0102568 A1 * | 4/2014 | Servin | ................ | F16L 47/00 137/800 |
| 2017/0362938 A1 * | 12/2017 | Lucas | ................ | F04C 15/064 |

OTHER PUBLICATIONS

International Preliminary Report on Patentability, Application No. PCT/EP2016/057984, dated Jun. 23, 2017, 11 pages.

* cited by examiner

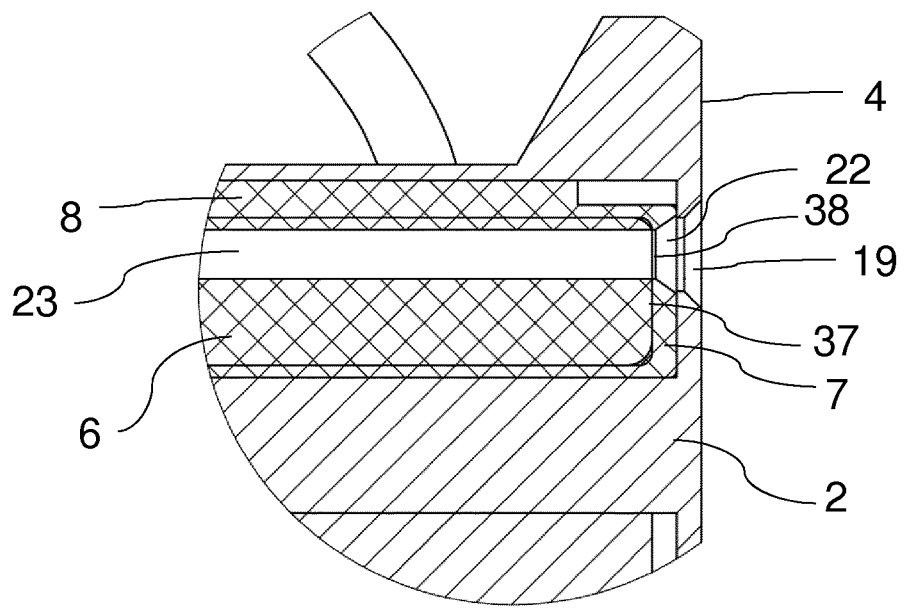
Fig. 5
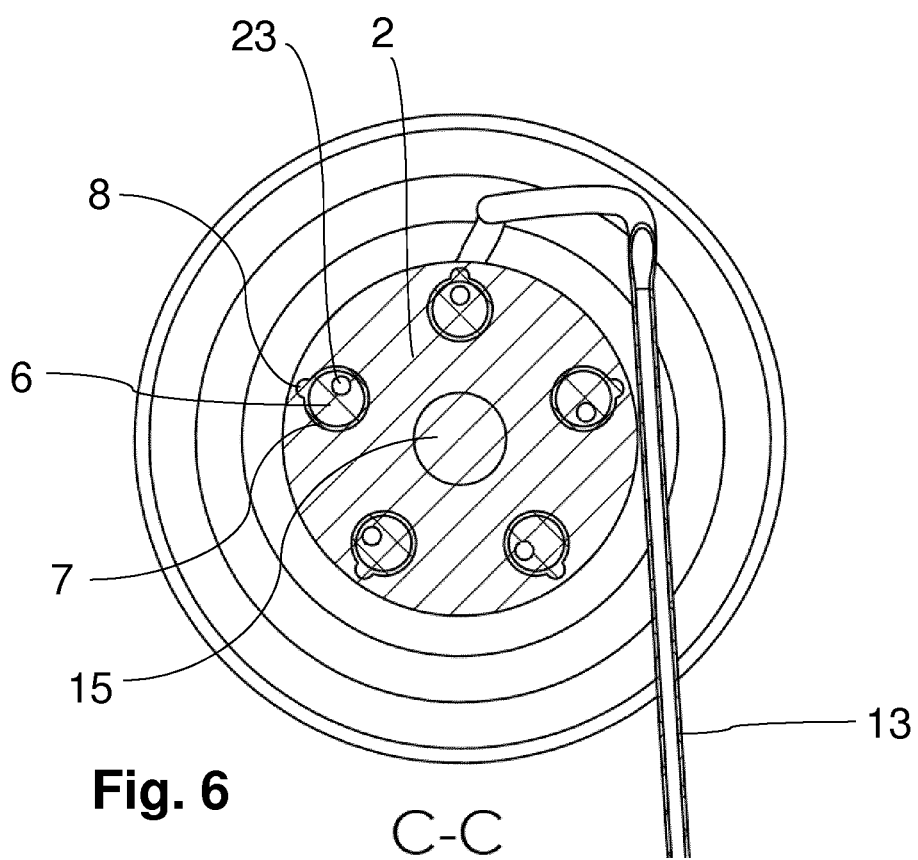
Fig. 6 C-C

D 3:1

SAMPLING DEVICE FOR WITHDRAWING FLUID SAMPLES FROM A FLUID CONTAINER

FIELD

The aspects of the disclosed embodiments relate to a sampling device for withdrawing a plurality of samples from a fluid container. In another aspect, the present invention relates to a method of withdrawing a sample from a fluid container and the use of cylindrical elements to that effect.

BACKGROUND

Aseptically withdrawing a plurality of fluid samples from a container is important in many industries such as in the pharmaceutical industry, food industry, breweries or biotech applications. Such industries use large tanks or containers preparing and treating liquids as well as dissolving and mixing components therein. These liquids may include aqueous pharmaceutical formulations or nutritional products such as beer or dairy products.

There is a need to sample such liquids throughout the manufacturing process to ensure quality control and process monitoring. This includes chemical, biological and/or physical analysis as well as screening for process intermediates for monitoring the progression of chemical reactions.

Typically, such containers comprise at least one opening into which a suitable valve, port or related mechanism can be fitted. The processing of the fluid, such as the production of pharmaceuticals, is then typically conducted under closed conditions. Microbiological or biochemical reactions such as fermentations require an aseptically isolated space within a bioreactor from which samples have to be withdrawn and analysed for monitoring status and progress of reactions.

An aseptic and reproducible sampling of a plurality of samples from such containers remains a technical challenge. Commonly known devices use fittings welded to the container with one or more valves attached to the fitting. One or more liquid samples may be withdrawn through flexible tubes and attached sampling bags, bottles or any receptacle. Liquid remaining in the valve may be transferred to subsequent samples or may give rise to bacterial contamination. In addition, several known sampling systems require the piercing of a septum with a hypodermic needle with the associated disadvantages, which include introducing a foreign item or particles from the membrane into the process.

WO 2007/143426 A2 relates to a sampling device with a sanitary fitting having a first port, and a rotatable sample coupling with two or more second ports. Rotating the sample coupling causes the first port to sequentially align with each of the second ports, thus allowing fluid access through the aligned first and second ports.

U.S. Pat. No. 5,823,222 A discloses a sampling system comprising a nipple with a coupling means, the nipple providing a fluid channel. The coupling means seals the nipple while a stopping means engages the coupling means to permit flow of the fluid. The fluid flows through the coupling means into a sterile sample container. The nipple and the coupling means are subsequently disengaged and the flow is terminated by the stopping means. In a final step, the coupling means is cleaned prior to further sampling.

EP 1548420 B1 relates to a fluid sampling device with a port insert having several channels receiving elongated members for selectively opening and closing the channels by linear displacement. The elongated members carry a cap at their distal ends for preventing undesired pulling out of the members from the channels.

US 2008/022785 A1 discloses a fluid sampling device with a first member having a plurality of channels, and a second member having a through passage, wherein the first member and said second member are rotatable with respect to each other such that each of the channels of the first member can be sequentially aligned with the passage of the second member.

The above described prior art valves or fittings typically have a complicated design which presents important drawbacks and technical challenges as well as adding to the overall cost of production and operation. In addition, there is a risk of cross-contamination between different samples or old sample residues being carried over into later samples using the prior art systems.

In one aspect, the disclosed embodiments are directed to providing an improved sampling device for withdrawing a plurality of fluid samples from a container.

In another aspect, the disclosed embodiments are directed to providing a cost-efficient and simple design of a sampling device, thus facilitating the manufacturing and operation of said device.

In another aspect, the disclosed embodiments are directed to providing a sampling device design that minimises the risk of cross-contamination between fluid samples.

In another aspect, the disclosed embodiments are directed to providing a sampling device resulting in improved work safety and decreased risk of maloperation for operating staff.

In yet another aspect, the disclosed embodiments are directed to design an easily disposable sampling device.

In another aspect, the disclosed embodiments are directed to design a flexible sampling system allowing for the sampling of a variable amount of samples from a fluid container.

SUMMARY

In a first aspect, the disclosed embodiments relate to a sampling device for withdrawing a plurality of samples from a fluid container, the sampling device comprising:
 a support member for mounting into a port of a fluid container, the support member having a distal end surface facing the fluid when mounted into the port and an opposing proximal end surface, wherein the support member comprises a plurality of through passages extending between the distal end surface and the proximal end surface, wherein each through passage comprises a first channel connecting to a second channel within the support member, the first channel extending from the proximal end surface and the second channel extending from the distal end surface, wherein the second channel is arranged eccentrically with respect to the first channel;
 a plurality of elongated inserts, each insert comprising a cylindrical distal part rotatably arranged in one of the first channels of the support member and having a distal end surface, and a proximal part protruding beyond the proximal end surface of the support member, wherein each insert comprises a through conduit forming an eccentric aperture within the distal end surface of the cylindrical distal part, the through conduit being alignable and misalignable with the second channel of the respective through passage of the support member by rotating the insert relative to the support member.

In other words, the aspects of the disclosed embodiments relate to a sampling device for withdrawing a plurality of samples from a fluid container, the sampling device comprising:

a support member for being mounted into a port of a fluid container, the support member having a distal end surface facing the fluid when mounted into the port and an opposing proximal end surface, wherein the support member comprises a plurality of through passages extending between the distal end surface and the proximal end surface, wherein each through passage comprises a first channel extending from the proximal end surface and a second channel extending from the distal end surface and arranged eccentrically with respect to the first channel, the first channel connecting within the support member to the second channel, a plurality of elongated inserts, each insert comprising a cylindrical distal part rotatably arranged in one of the first channels of the support member and having a distal end surface, and a proximal part protruding beyond the proximal end surface of the support member, wherein each insert comprises a through conduit forming an eccentric aperture within the distal end surface of the cylindrical distal part, the through conduit being alignable and misalignable with the second channel of the respective through passage of the support member by rotating the insert relative to the support member.

In a preferred embodiment, the distal and proximal end surfaces of the support member have a substantially circular shape. Preferably, the support member is a substantially cylindrical body such that its distal and proximal end surfaces form respective substantially circular cylinder surfaces. The cylindrical shape may have variable diameters along its length, such as a first diameter along part of its length and a second, larger diameter along another part of its length. In particular, the substantially circular distal end surface may have a larger diameter than the substantially circular proximal end surface.

It is preferred that the through passages extending between the distal end surface and the proximal end surface are arranged axially with respect to the centre axis of the support member (such as a centre axis of a substantially cylindrical body), i.e. substantially parallel to the centre axis of the support member. Preferably, the through passages extend substantially perpendicular to the distal and the proximal end surfaces. In other words, the centre axis of the support member, the first channel and the second channel may all point in the same direction in space. As mentioned above, each through passage comprises a first channel and a second channel. Preferably, the longitudinal axis of the first channel is parallel to the longitudinal axis of the second channel such that both channels extend substantially perpendicular to the distal and the proximal end surfaces.

In a preferred embodiment, the through passages are regularly arranged in a circle surrounding the centre axis of the support member, i.e. arranged with an even angular distance. The through passages will typically be straight. The first channels will typically have a cylindrical cross section.

Advantageously, the first channel extends through at least 70%, more preferably at least 80%, most preferably at least 90% or 95% of the thickness of the support member. Correspondingly, the second channel may extend through 30% or less, 20% or less, or 10% or less, or 5% or less of the thickness of the support member. The thickness of the support member is the shortest linear distance between its distal and proximal end surfaces. If the support member has a substantially cylindrical form, the thickness corresponds to the cylinder height.

The first channel is preferably substantially cylindrical, i.e. has a circular cross section, optionally comprising an axially extending groove along at least part of its length. The second channel may have a cylindrical shape, a conical shape or a frustoconical shape.

It is preferred that the second channel is narrower than the first channel, i.e. that the second channel has a smaller cross-sectional flow area along its entire length than the first channel. Advantageously, the largest diameter of the second channel does not exceed 50%, more preferably 40%, most preferably 30% of the largest diameter of the first channel. It is particularly preferred that the largest diameter of the second channel is less than the 50% of the diameter of the first channel.

In a preferred embodiment, the centre axis of the first channel does not intersect with the cross section of the second channel.

At the point of connection between the first channel and the second channel within the support member the cross section of the second channel will typically lie completely within the cross section of the first channel, albeit not concentrically.

The elongated inserts may be directly arranged in the respective first channels or they may be received via a sleeve, sheath or the like, which is placed within the respective first channels. Such sleeve or sheath is preferably hollow with a cylindrical inner space for receiving the distal part of an insert. The outer shape of the sleeve will typically match the shape of the first channel, e.g. it will be cylindrical if the first channel is cylindrical.

Preferably, the proximal part of the insert is adapted for attachment to a flexible tube which in turn leads to a sampling receptacle for receiving a sample withdrawn from the container. In one embodiment, the proximal part of the insert comprises a cylindrical or arcuate toothed section and a tubular section for attachment to a flexible tube. In another embodiment, the proximal part of the insert comprises an arcuate toothed section and a tubular section for attachment to a flexible tube, wherein the tubular section extends radially from the insert body. The toothed section is preferably adjacent to the distal part of the insert. The toothed section may be formed by a completely or partially toothed cogwheel or a cylindrically shaped part.

The proximal part of each insert protrudes beyond the proximal end surface of the support member when the inserts are arranged in the latter. Preferably, the diameter of the cylindrical distal part of the insert is at least three times, more preferably at least four times, most preferably at least five times larger than the diameter of the eccentric aperture.

Preferably, at least part of the through conduit of the insert extends axially through the insert. The through conduit may extend axially throughout the length of the insert. The through conduit may also comprise one or more curves, corners, or angles. In one embodiment, part of the through conduit extends axially, whereas another part of the through conduit extends radially with respect to the insert. In one embodiment, the insert is substantially cylindrical with a distal and a proximal end surface and an interconnecting side surface, wherein the through conduit extends from the eccentric aperture in the distal end surface to a point in the side surface of the insert.

Preferably, the cylindrical distal part accounts for more than 50%, more preferably more than 70%, most preferably more than 80% of the total length of the elongated insert. It has been found that such dimensions ensure increased stability and prevention of inadvertent removal of inserts from the support member.

The distal end surface of the cylindrical distal part will typically be circular. The eccentric aperture is formed within this circular surface at a location other than the centre of the circular distal end surface.

In one embodiment, the through conduit of the insert is cylindrical with a circular cross section. The diameter of the through conduit may be less than one third, less than one fourth, or less than one fifth of the diameter of the cylindrical distal part of the insert.

As discussed above, the eccentric aperture, and thereby the through conduit, is alignable and misalignable with the second channel of the respective through passage of the support member by rotating the insert relative to the support member.

The sampling device of the disclosed embodiments preferably comprises more than two, more preferably more than three, most preferably more than four or more than five elongated inserts and corresponding through passages in the support member. This allows for sampling increased numbers of individual samples from a fluid container as compared to prior art systems. Since the system of the present invention uses one individual insert per sample withdrawal, the risk of cross-contamination between individual samples is virtually absent. The risk of cross contamination is also greatly reduced due to the combination of an individual insert and an individual second channel, these two components jointly performing the valve action of the sampling device.

Prior to use, the sampling of device of the disclosed embodiments may be sterilised, preferably by gamma irradiation. Once the device is mounted to the port of the fluid container it may undergo cleaning-in-place (CIP) or sterilisation-in-place (SIP).

According to a preferred embodiment, the sampling device further comprises an actuation member for sequentially rotating each insert such that by unidirectional movement of the actuation member each of the inserts is sequentially rotated from a first position of misalignment, through a second position of alignment, to a third position of misalignment of the through conduit and the second channel. This design allows the use of one individual insert per sample without the necessity to independently operate different inserts. With the present invention, a single actuation member can be used for handling all inserts. This has the advantage of minimising user errors in selecting and handling individual pieces of the sampling device.

In a preferred embodiment, the actuation member is designed such that it cannot be moved, such as rotated, back beyond the third position of misalignment for each insert.

The actuation member may comprise a shaft, gear, cogwheel and/or arcuate portion having one or more teeth or cogs which mesh with a toothed section of the elongated inserts. The shaft may have a varying diameter along its length. In a particularly preferred embodiment, the actuation member comprises a shaft carrying a cogwheel. In such embodiments the through passages, and accordingly the inserts, may be arranged in a circle, as seen from the proximal end surface of the support member, and the actuation member may be arranged at the centre of said circle. Alternatively, the actuation member may be a linearly displaceable member comprising one or more teeth, wherein the through passages and accordingly the inserts may be arranged linearly, i.e. substantially in a row.

The actuation member may also comprise a handle. Preferably, the actuation member is rotatable and comprises an arcuate toothed portion and a handle. In one embodiment, the actuation member comprises a partially toothed cogwheel and a handle.

According to a preferred embodiment of the present disclosure, the proximal part of each insert comprises a toothed section, and the actuation member comprises one or more teeth for sequentially engaging with the toothed section of each insert. The toothed section may be provided around at least part of the circumference of a cylindrical element of the proximal part of the insert. Such element may be a completely or partially toothed cogwheel. Likewise, the one or more teeth on the actuation member may be provided on a cylindrical element of the actuation member such as a shaft, a cogwheel, a gear, an arcuate portion or the like.

According to a preferred embodiment, the sampling device further comprises a sleeve mounted within the first channel of the through passage for rotatably receiving the distal part of the insert in the sleeve. Such sleeve or sheath is preferably hollow with a cylindrical inner space for receiving the distal part of an insert. The outer shape of the sleeve will typically match the shape of the first channel, e.g. it will be cylindrical if the first channel is cylindrical. Preferably, a sleeve is mounted in each first channel of each through passage. This enables an easier fitting of the insert within the support member and allows for receiving inserts of different diameter by adapting the wall thickness of the sleeve accordingly. A sleeve may also provide sealing to prevent inadvertent leakage. Another advantage of using a sleeve for receiving the inserts in the support member is that the material of the sleeve may easily be adapted or changed to increase or decrease friction between insert and sleeve, thus adapting the force necessary to rotate the inserts.

In a preferred embodiment, the sampling device comprises a first sealing element between the distal end of the sleeve and the distal end surface of the first channel. This first sealing element may be an integral part of the sleeve, such as a circular distal end surface. In addition, the sampling device may comprise a second sealing element between the distal end surface of the insert and the first sealing element, or between the distal end surface of the insert and the internal bottom surface of the sleeve. This second sealing element may be an integral part of the insert. The sealing and the insert may be moulded together in a 2K moulding. The sealing elements may be sealing washers, discs or the like.

The sleeve may comprise a circular distal end surface comprising an orifice which is alignable with the second channel of the support member. This may further increase tightness and improve sealing. Preferably, such sleeve is mounted in each first channel of the through passage of the support member. The circular distal end surface of the sleeve may abut tightly against the corresponding distal end surface of the first channel. This ensures improved sealing. Advantageously, the sleeve is designed such that a tight fit is ensured around the orifice.

According to a preferred embodiment, the sleeve comprises a protrusion on its outer surface, wherein the first channel of the through passage comprises a longitudinally extending groove adapted to receive the protrusion of the sleeve for preventing rotation of the sleeve relative to the support member. Preferably, the protrusion is a linear element, such as ridge, extending longitudinally along at least part of the outer surface of the sleeve. This will increase stability and prevent rotation of the sleeve relative to the support member. The protrusion/groove arrangement may also help to identify the circular position of the respective second channel relative to the first channel if, for example, the groove is always placed at the same circular position as the second channel with respect to the first channel. Hence, a user may visually determine the circular position of the second channel by way of the groove/protrusion even if the inserts are already installed in the first channels of the support member.

According to another embodiment, the actuation member is rotatable and comprises an arcuate toothed portion for sequentially engaging with the toothed section of each insert such that by unidirectional rotation of the actuation member each of the inserts is sequentially rotated from a first position of misalignment, through a second position of alignment, to a third position of misalignment of the through conduit and the second channel. The arcuate toothed portion may be provided by a partially toothed cogwheel. This greatly simplifies the handling of the inventive sampling device since all inserts are sequentially rotated by a single, unidirectional motion of the actuation member. Also, the inventive system ensures that each sampling channel, i.e. second channel, is closed before a new sampling channel is opened. This effectively eliminates the risk of sample cross-contamination. It also eliminates operator errors. The actuation member may be secured to the support member by a centre screw, nut or the like.

The actuation member may further comprise a shaft which is preferably arranged perpendicular to the proximal end surface of the support member. Advantageously, the shaft is concentrically and rotatably received within the support member such that the longitudinal axis of the shaft coincides with the central axis of the support member; i.e. the centre axis perpendicular to the distal and proximal end surfaces of the support member.

The shaft may have varying diameters along its length such as a larger diameter towards its proximal end and a smaller diameter towards its distal end. In a preferred embodiment, the actuation member comprises a partially toothed cogwheel, optionally mounted on a shaft. Said partially toothed cogwheel and the shaft may be formed as a single piece.

Alternatively, the support member may comprise a rod extending perpendicularly from its proximal end surface, wherein the rod is received within a central bore of the actuation member such that the latter can rotate relative to the support member. Said rod may further comprise an outer thread at its proximal end for fastening to a nut to prevent axial movement of the actuation member relative to the support member.

In a preferred embodiment, the rod of the support member comprises a radially extending protrusion which fits into a linear groove within the actuation member, wherein said linear groove leads to an annular groove within the actuation member. This ensures that the actuation member is mounted on the support member in a predefined rotational position defined by the linear groove. Once the actuation member is mounted on the support member, the actuation member may rotate unidirectionally relative to the support member while the protrusion of the rod moves within the annular groove of the actuation member. Following a full 360° rotation, the actuation member may then be removed as the protrusion moves within the linear groove of the actuation member.

In a particularly preferred embodiment, the actuation member comprises a distally facing annular rim for abutting against a surface, preferably a proximally facing surface, of the proximal part of each elongated insert to prevent axial movement of the inserts relative to the support member when the actuation member is mounted on the support member. Preferably, said annular rim is formed adjacent to the arcuate toothed portion of the actuation member. Advantageously, the untoothed section of the partially toothed cogwheel has a smaller diameter than the proximally adjacent annular rim. It is preferred that said annular rim abuts at least part of the toothed section of each insert such that axial movement of the inserts relative to the support member is prevented when the actuation member is in place.

In an advantageous embodiment, the sampling device comprises one or more breakable shear pins or snap locks preventing rotation of the insert relative to the support member prior to breaking the shear pin or snap lock. Advantageously, relative rotation of the insert is only possible when the actuation member breaks the snap lock or shear pin as it engages the toothed section of the insert.

Preferably, the support member comprises a central cavity formed within its proximal end surface, wherein the distal end of a shaft of the actuation member is received in the central cavity of the support member. Alternatively, the actuation member comprises a central cavity or bore to receive the proximal end of a rod of the support member extending perpendicularly from the proximal end surface of the support member. Either way, the support member and the actuation member are preferably arranged concentrically to each other.

In a preferred embodiment, the arcuate toothed portion has an arc length corresponding to an angle of 10-65°.

In an advantageous embodiment of the present disclosure, the actuation member comprises a handle for manually rotating the actuation member. Actuation of the actuation member can also be done automatically, e.g. by pneumatically controlled activation.

Preferably, the handle comprises external labelling to relate the relative rotational position of the actuation member to the alignment of the second channel and the through conduit of each respective insert.

In another embodiment of the present invention, the actuation member is only rotatable in one direction. This has been found by the present inventors to be particularly useful for preventing user errors, i.e. inadvertent re-sampling or opening of second channels. For example, the actuation member may be rotatable only counter clockwise as seen from the proximal end of the sampling device, i.e. as seen by the user, while clockwise rotation is mechanically prevented. This can be achieved, for example, by using a ratchet mechanism, rotational stops or the like. To this end the actuation member may comprise a collar carrying a number of asymmetrical teeth, each tooth having a moderate slope on one edge and a steeper slope on the other edge. The collar is advantageously facing distally. When the actuation member is mounted on the support member the asymmetrical teeth of the collar may engage with a spring or a spring-loaded finger on the support member to allow rotary motion of the actuation member only in one direction. In an alternative embodiment, the collar may be placed on the support member and the spring or spring-loaded finger is placed on the actuation member.

In a preferred embodiment, each insert comprises a breakable shear pin to prevent rotation of the insert relative to the support member until the shear pin is broken. Said shear pin may be received in a corresponding hole in the sleeve or in the support member.

According to another embodiment, the proximal part of each insert is connected to tubing leading to a respective sample receptacle. To this end, the proximal part may comprise a tubular element onto which a tube may be imposed.

According to an advantageous embodiment, the sampling device comprises no needles or cannulas.

According to a preferred embodiment, the support member is substantially cylindrical, and the distal and proximal end surfaces of the support member form respective substantially circular cylinder surfaces, wherein the through passages are regularly arranged around the central axis of the substantially cylindrical support member. Preferably, the through passages are arranged in a circle with a regular mutual distance between neighbouring through passages. If, for example, five through passages are provided in the support member the through passages may be arranged in a circle, each passage being separated by an arc length corresponding to about 72°.

It is preferred that one or more components of the sampling device are for single use only. In one embodiment, all parts of the sampling device are made from plastic. This has the advantage that no metal parts are included and the device can be easily disposed of. The support member and the actuation member may be for single use or re-usable.

If a number of samples is needed which is lower than the number of through passages in the support member it is advantageous to insert one or more blind inserts into the respective first channels instead of the elongated inserts. In this way, the number of samples can be adapted beforehand to accommodate for the requirements at hand. A blind insert may correspond to the shape of the elongated insert, albeit without having a through conduit.

In another aspect, the disclosed embodiments relate to a method of withdrawing a plurality of samples from a fluid container. The method comprises the steps of a) mounting a support member into a port of a fluid container, the support member having a distal end surface facing the fluid when mounted into the port and an opposing proximal end surface, wherein the support member comprises a plurality of through passages extending between the distal end surface and the proximal end surface, wherein each through passage comprises a first channel connecting to a second channel within the support member, the first channel extending from the proximal end surface and the second channel extending from the distal end surface, wherein the second channel is arranged eccentrically with respect to the first channel;

b) rotatably arranging a plurality of elongated inserts in respective first channels of the support member, each insert comprising a cylindrical distal part for rotatably arranging the insert in one of the first channels of the support member and having a distal end surface, and a proximal part protruding beyond the proximal end surface of the support member when the distal part is arranged in the first channel, wherein each insert comprises a through conduit forming an eccentric aperture within the distal end surface of the cylindrical distal part, c) rotating a first insert relative to the support member from a first position of misalignment of the through conduit and the second channel, to a second position of alignment of the through conduit and the second channel, d) withdrawing a liquid sample from the container through the aligned second channel and through conduit, e) further rotating the first insert in the same direction to misalign the through conduit and the second channel, f) carrying out steps c) to e) with at least a second insert arranged in the support member.

Preferably, steps c) to e) are sequentially carried out with at least three inserts arranged in the support member to withdraw at least three samples from the fluid container.

Typically, step a) is carried out after step b). Usually, the different samples are taken at different points in time during a single production batch.

In another embodiment of the method, steps a)-e) are preceded by cleaning-in-place (CIP) and/or sterilising-in-place (SIP) of the support member and/or the inserts.

In one embodiment, the method includes placing at least one blind insert having no through conduit into a respective first channel of the support member. This allows for a flexible adaption to the anticipated number of samples to be taken in cases where the number of through passages exceeds the number of required samples.

A sampling receptacle connected to the elongated insert by a tube may be separated after sampling withdrawal by cutting and sealing the tube as generally known in the art.

In another aspect, the disclosed embodiments relate to the use of a plurality of cylindrical elements for withdrawing a plurality of samples from a fluid container having a port fitting rotatably receiving said cylindrical elements, each element having a distal end surface and containing a through conduit forming an eccentric aperture within the distal end surface of the cylindrical element, wherein the through conduit is rotationally alignable and misalignable with a respective channel in the port fitting being in fluid communication with fluid in the container.

As used herein, the term "distal" means the location situated further from the user and the term "proximal" means the location situation nearer to the user when the sampling device is used to withdraw samples from a container. Accordingly, "distal" refers to the container side or the process liquid media side whereas "proximal" is the end nearer to the operator.

As used herein, the term "alignment" means that there is an overlap in cross-sectional flow area between the through conduit of the insert and the second channel of the through passage of the support member, thus allowing for fluid communication between both elements. The term "misalignment" means that there is no overlap in cross-sectional flow area between the through conduit of the insert and the second channel of the through passage of the support member, thus preventing fluid communication between both elements. The same applies to the terms "alignable" and "misalignable".

As used herein, the term "eccentric" means that two respective elements, such as a distal end surface and an aperture formed therein, do not share a common centre, i.e. that the elements are not concentric. Consequently, the term "eccentric aperture" means that the aperture is not arranged centrically within the distal end surface but at a location other than the centre of the surface. Similarly, a second channel arranged eccentrically with respect to a first channel means that the channels are not concentric, i.e. do not share a common centre axis.

As used herein, "longitudinal" describes a direction along the length of the respective element, such as an elongated insert.

FIGURES

Figure 2:
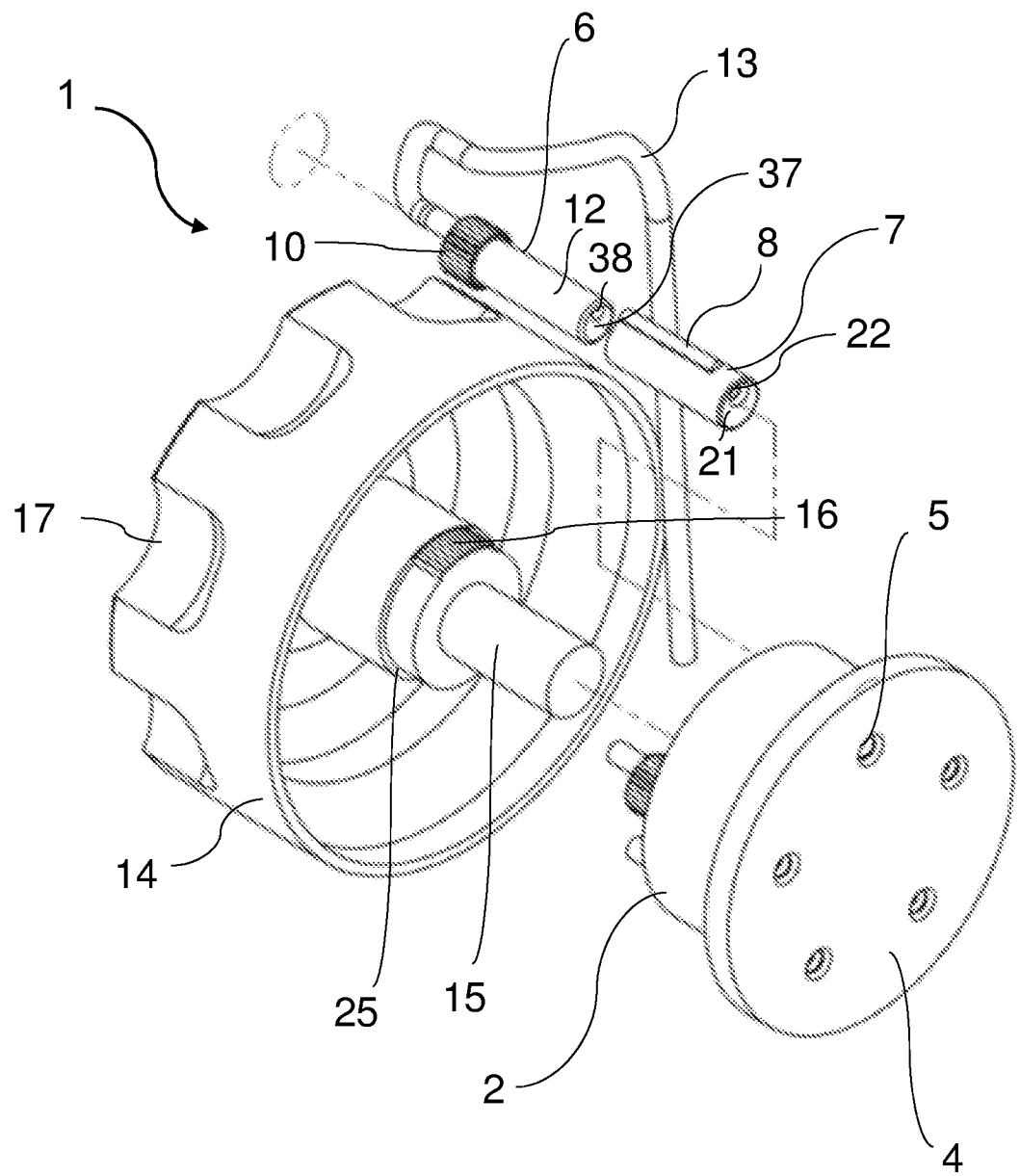
Figure 3:
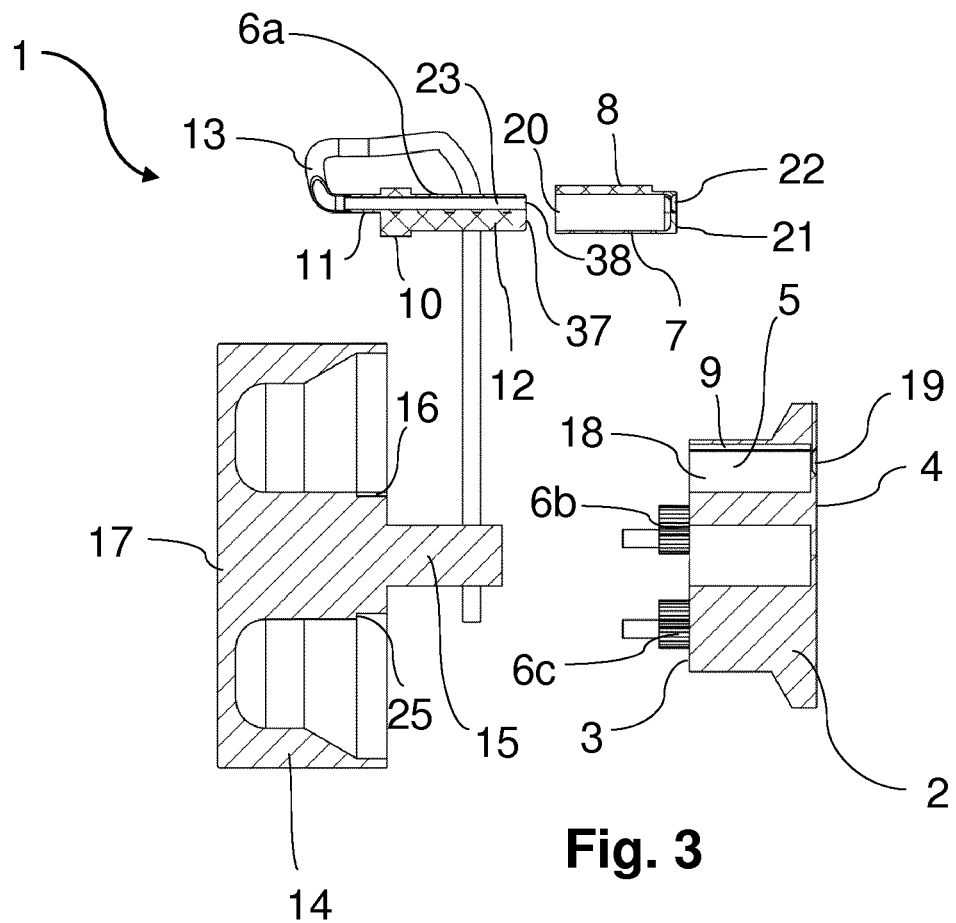
Figure 4:
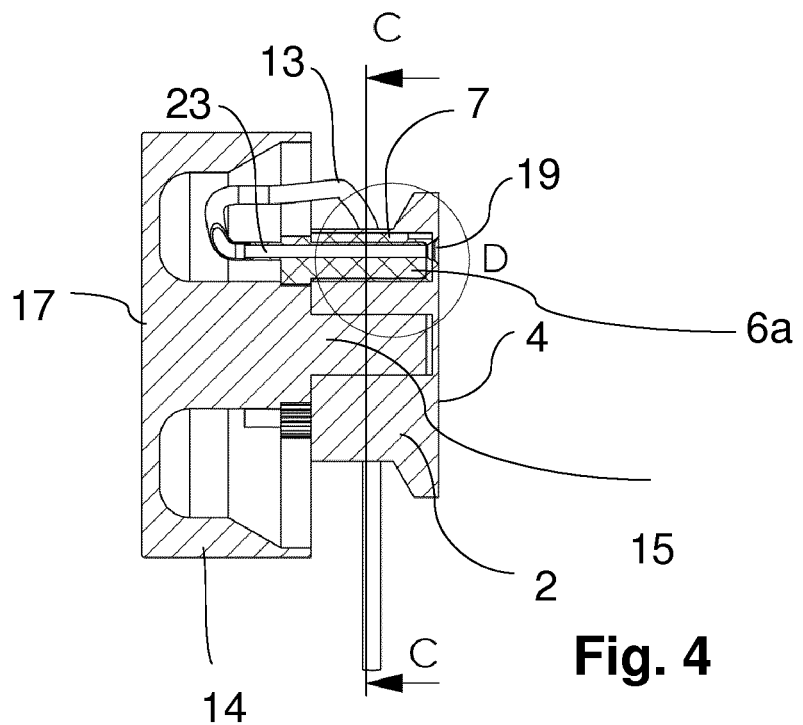

A few exemplary embodiments of the present disclosure will be described in more detail in the following with reference to the figures, of which FIG. 1 is an exploded perspective view of a sampling device according to an aspect of the disclosed embodiments shown from the proximal end, FIG. 2 is an exploded perspective view of a sampling device according to an aspect of the disclosed embodiments, shown from the distal end, FIG. 3 is an exploded sectional view of the sampling device of FIGS. 1 and 2 cut along its centre, FIG. 4 is an assembled sectional view of the sampling device of FIG. 3, FIG. 5 is an enlargement of the part of FIG. 4 marked with the circle "D", FIG. 6 is a cross-sectional view taken along line C-C in FIG. 4, and FIG. 7 is a see-through view shown from the distal end of the sampling device according to an aspect of the disclosed embodiments.

Figure 8:
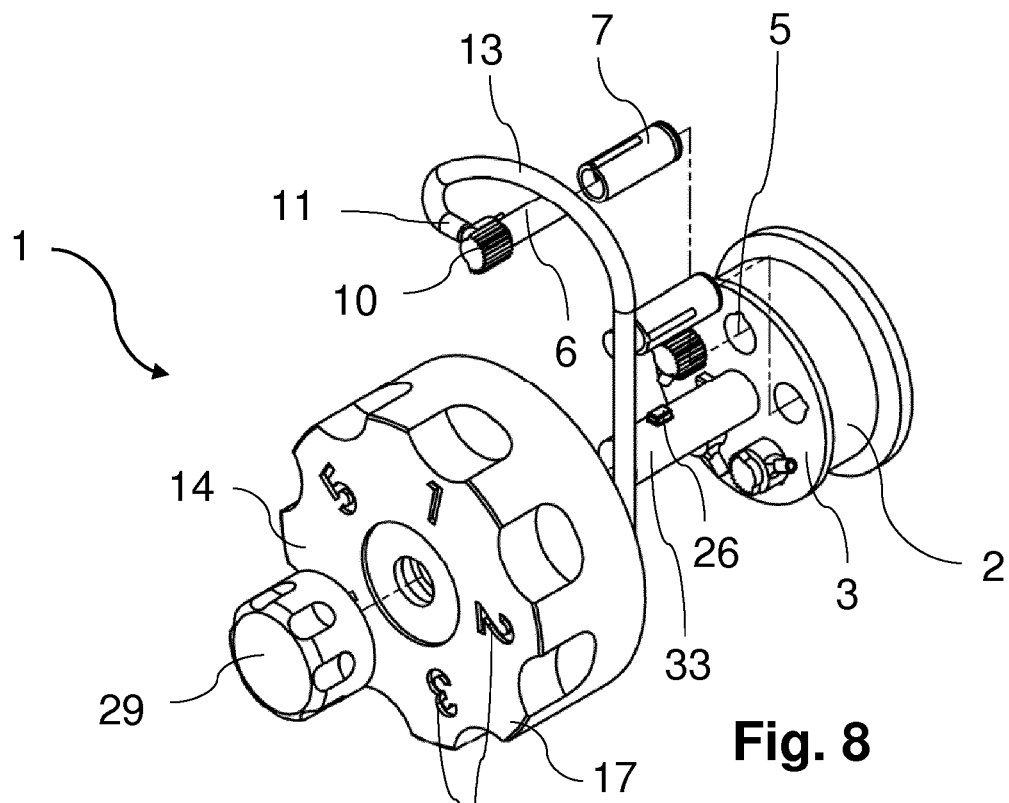
Figure 9:
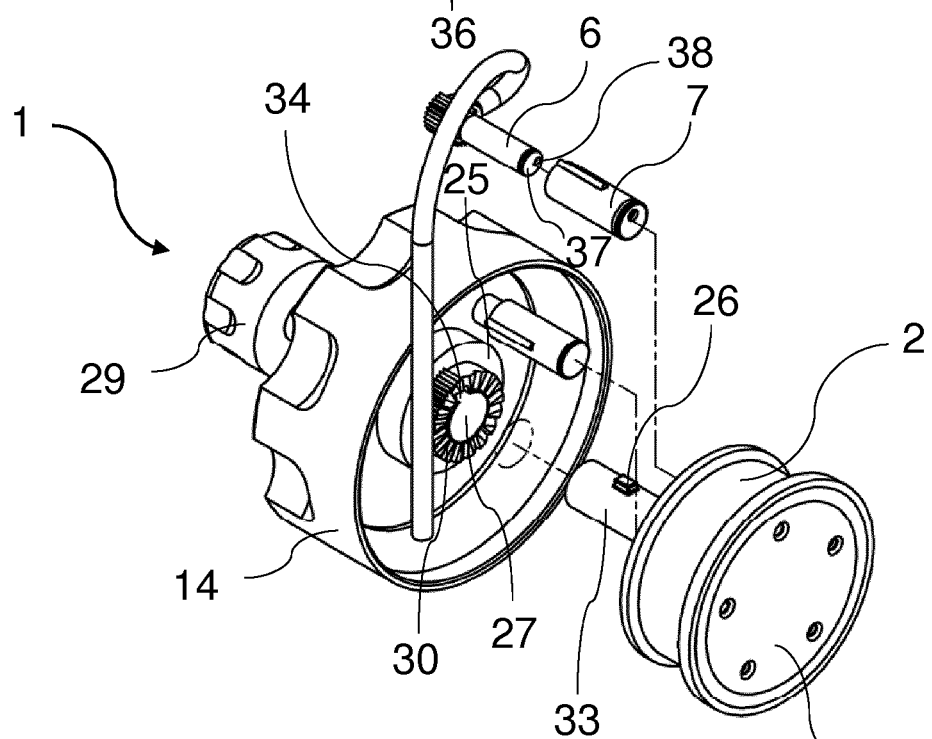

FIG. 8 is an exploded perspective view of another embodiment of a sampling device according to the present disclosure, shown from the proximal end, FIG. 9 is an exploded perspective view of the sampling device of FIG. 8, shown from the distal end, and FIG. 10 is an assembled sectional view of the sampling device of FIGS. 8 and 9 cut along its centre.

DETAILED DESCRIPTION

In a preferred embodiment, the aspects of the present disclosure relate to a sampling device for withdrawing a plurality of samples from a fluid container, the sampling device comprising:

a support member for mounting into a port of a fluid container, the support member having a distal end surface facing the fluid when mounted into the port and an opposing proximal end surface, wherein the support member comprises a plurality of through passages extending between the distal end surface and the proximal end surface, wherein each through passage comprises a first channel connecting to a second channel within the support member, the first channel extending from the proximal end surface and the second channel extending from the distal end surface, wherein the second channel is arranged eccentrically with respect to the first channel;

a plurality of elongated inserts, each insert comprising a cylindrical distal part rotatably arranged in one of the first channels of the support member and having a distal end surface, and a proximal part protruding beyond the proximal end surface of the support member and comprising a toothed section, wherein each insert comprises a through conduit forming an eccentric aperture within the distal end surface of the cylindrical distal part, the through conduit being alignable and misalignable with the second channel of the respective through passage of the support member by rotating the insert relative to the support member;

a rotatable actuation member comprising an arcuate toothed portion for sequentially engaging with the toothed section of each insert for rotating each insert such that by unidirectional movement of the actuation member each of the inserts is sequentially rotated from a first position of misalignment, through a second position of alignment, to a third position of misalignment of the through conduit and the second channel.

As can be seen in the perspective drawings of FIGS. 1 and 2, a sampling device 1 according to the disclosed embodiments comprises a support member 2 with a plurality of inserts 6a-e received therein. The support member has a proximal end surface 3 (see FIG. 1), which is closer to the operator when the sampling device is mounted into the port of a fluid container (not shown), and a distal end surface 4 (FIG. 2) facing the fluid in the container. The support member 2 comprises a number of through passages 5. As is best seen in the cross-sectional view of FIG. 3, each through passage 5 comprises a first channel 18 and a second channel 19, which are connected at a point within the support member 2. In the depicted embodiment, the second channel 19 has a smaller diameter than the first channel 18 and is arranged eccentrically to the same.

In the embodiment shown in FIG. 1, the support member 2 also comprises a central cavity 24 for receiving a shaft 15 of an actuation member 14. With this arrangement the actuation member 14 can be rotatably mounted to the support member 2 to allow rotation of the former relative to the latter.

The inserts 6 comprise a cylindrical distal part 12 which is received in the first channel 18 of the support member 2 via a sleeve 7. The cylindrical distal part 12 comprises a circular distal end surface 37. (see e.g. FIG. 2). The inserts 6 also comprise a proximal part with a toothed section 10 and an adjacent tubular section 11 for connection to a flexible tube 13. As is best seen in FIGS. 2 and 3, each insert has an axially extending through conduit 23 forming an eccentric aperture 38 in the circular distal end surface 37. The through conduit 23 is alignable with the second channel 19 of the respective through passage 5.

The sampling device 1 also comprises an actuation member 14 comprising a shaft 15 of varying diameter and an arcuate toothed portion 16 for sequentially engaging with the toothed section 10 of each insert 6. The actuation member 14 also comprises a handle 17 for manually rotating the actuation member. As is seen in the cross-sectional view of FIGS. 3 and 4, the actuation member is manufactured as single piece comprising the shaft 15, the arcuate toothed portion 16 and the handle 17. However, in other embodiments, the actuation member 14 may be made from different connected parts such as a separate shaft and a partially toothed cogwheel. As seen in FIG. 2, the section of the shaft proximally adjacent to the arcuate toothed portion 16 has a diameter exceeding the diameter of the untoothed section of the cog to form an annular rim 25 overlapping with the proximal part of each insert such that axial movement of the inserts relative to the support member is prevented. The overlap is best seen in FIG. 7a.

FIGS. 5 and 6 illustrate the rotatable arrangement of the inserts 6 in the support member 2 via sleeve 7. The sleeve 7 has a protrusion 8 which fits into a corresponding groove 9 of the first channel 18 of the through passage 5 of the support member 2 (see also FIG. 1). In this way the sleeve 7 cannot rotate relative to the support member 2. The groove 9 is located such that when inserting the sleeve 7 into the first channel 18 the orifice 22 in the distal end surface 21 of the sleeve 7 is aligned with the second channel 19 of the through passage. This is best seen in FIG. 5. The sleeve has a proximal opening 20 for rotatably receiving the cylindrical distal part 12 of the insert 6.

Figure 7A:
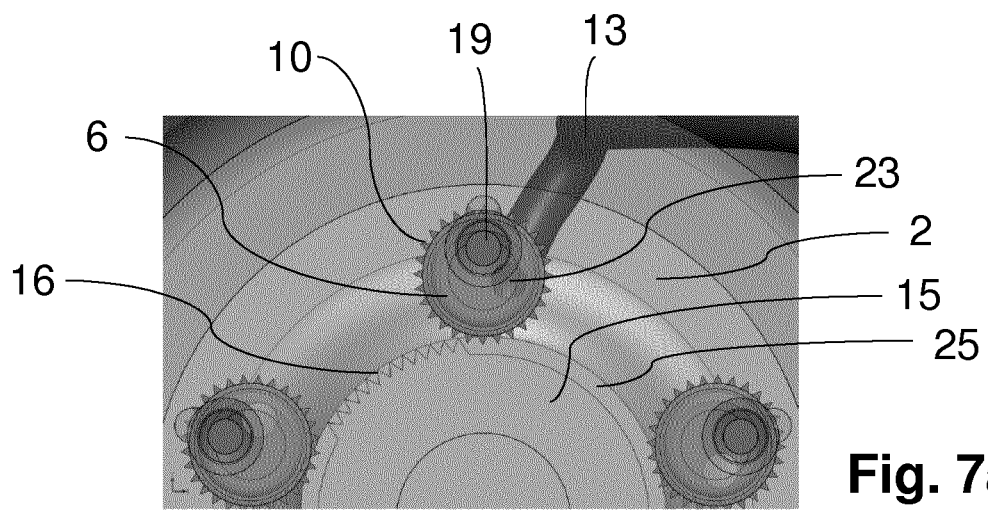
Figure 7B:
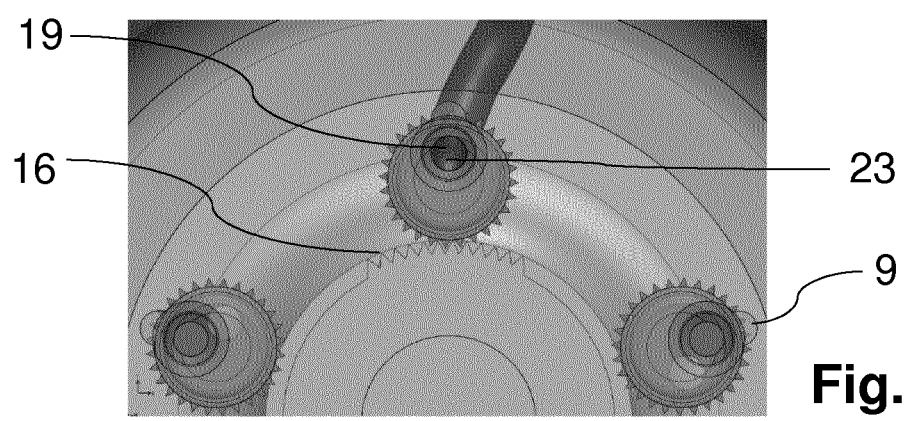
Figure 7C:
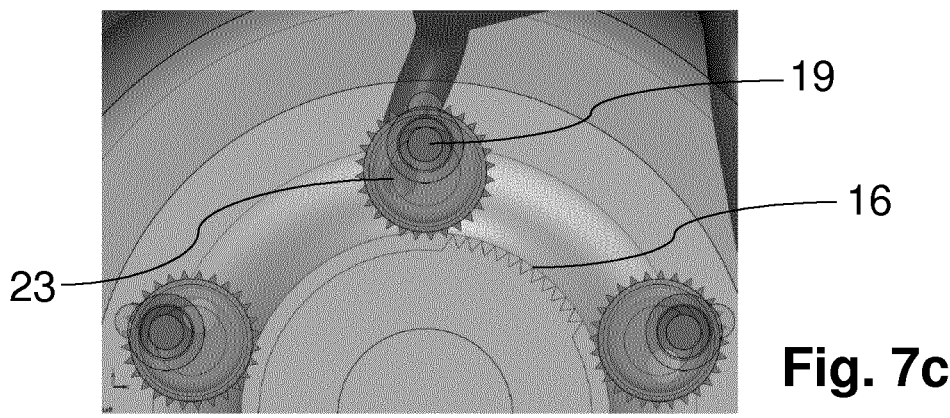

FIGS. 7a-7c illustrate the operation of the sampling device according to the aspects of the disclosed embodiments seen from the distal end, i.e. from the fluid container side. In a first position (FIG. 7a), there is no fluid passage between the container and the flexible sampling tube and attached sampling receptacle since the through conduit 23 of the insert 6 is misaligned with the second channel 19 of the through passage of the support member 2. The shaft 15 is then rotated so that its teeth 16 engage with the toothed section 10 of the insert 6 to bring the through conduit 23 and the second channel 19 into alignment (FIG. 7*b*). In this position, there is fluid communication between the insert and the container which allows withdrawing a sample through the conduit 23 into the flexible tube 13 and into a suitable sample receptacle (not shown).

When the sample has been withdrawn, the shaft 15 is further rotated in the same direction until its teeth 16 no longer engage the toothed section 10 of the insert 6 (FIG. 7*c*). The fluid passage is now again closed due to misalignment of the through conduit 23 and the second channel 19 of the through passage of the support member 2. By even further rotating the shaft 15 the next insert can be engaged and sequentially rotated from a first position of misalignment to a second position of alignment to a third position of misalignment (not shown). This sequential opening and closing of sampling channels virtually eliminates the risk of cross-contamination between samples and from previous samples.

FIGS. 7*a-c* also show another advantageous feature of the inventive sampling device. The circular position of the groove 9 matches the circular position of the second channel 19 relative to the first channel 18. In this way, the user can easily determine the circular position of the second channel 19 even when the inserts are already installed in the support member. This allows for an easy and user-friendly way of positioning the inserts prior to sampling.

Figure 10A:
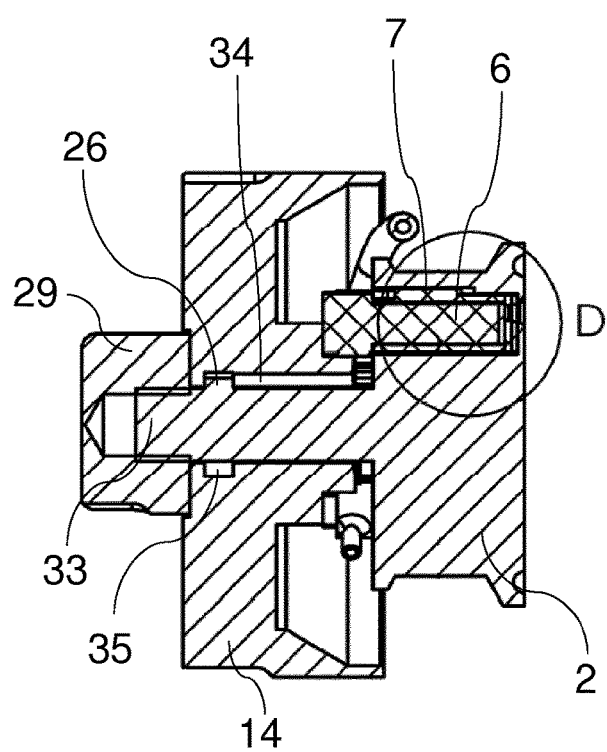

FIGS. 8-10 show another embodiment of the sampling device 1 of the disclosed embodiments. Here, the support member 2 comprises a rod 33 extending perpendicularly from its proximal end surface 3. The rod 33 is received within a central bore 27 of the actuation member 14 allowing the actuation member 14 to rotate relative to the support member. The rod 33 comprises an outer thread at its proximal end for fastening to a nut 29 to prevent axial movement of the actuation member 14 relative to the support member. The rod 33 also comprises a protrusion 26 which fits into a linear groove 34 within the actuation member 14. As seen in FIG. 10*a*, the linear groove 34 leads to an annular groove 35 within the actuation member 14. This embodiment allows arranging the actuation member 14 on the support member 2 only in one predefined rotational position. Once both elements are correctly assembled, the actuation member 14 may rotate relative to the support member 2 while the protrusion 26 moves within the annular groove 35. Following a full 360° rotation, the actuation member 14 may then be disassembled from the support member 2 while the protrusion 26 moves within the linear groove 34.

In the embodiment shown in FIG. 9, the actuation member 14 further comprises a collar 30 carrying a number of asymmetrical teeth, each tooth having a moderate slope on one edge and a steeper slope on the other edge. When the actuation member is mounted on the support member 2 the collar 30 may engage with a spring or spring-loaded finger (not shown) on the support member 2 to allow rotary motion of the actuation member 14 only in one direction by a ratchet mechanism.

Figure 10B:
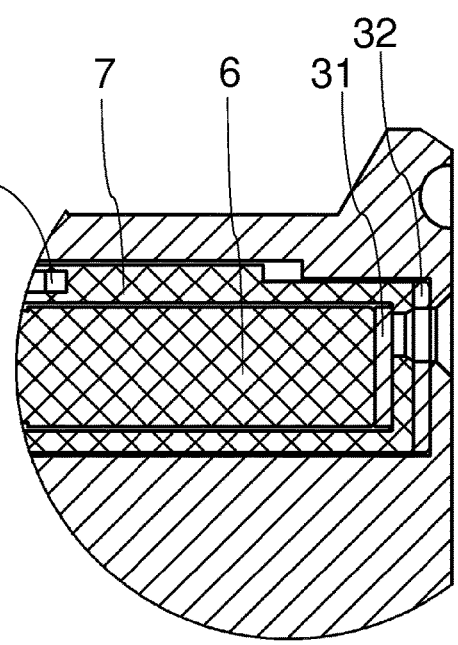

As best seen in FIG. 10*b*, the insert 6 comprises a breakable shear pin 28 received in a corresponding opening of the sleeve 7. This prevents rotation of the insert relative to the sleeve 7 and to the support member 2 before the shear pin 28 is broken by rotating the actuation member with a predefined force. As also seen in FIG. 10*b*, the sampling device comprises a first sealing element 32 between the distal end of the sleeve and the distal end surface of the first channel. In addition, the sampling device comprises a second sealing element 31 between the distal end surface of the insert and the first sealing element.

As shown in FIG. 8, the proximal part of each insert 6 comprises an arcuate toothed section 10 corresponding to an angle of about 180°. The proximal part of each insert 6 also comprises a tubular section 11 extending radially from the insert body for attachment to a flexible tube 13. As also shown in FIG. 8, the handle 17 comprises external labelling 36 to relate the relative rotational position of the actuation member 14 to the alignment of the second channel and the through conduit of each respective insert.

It will be understood by the skilled reader that the above-described embodiments are of exemplary nature only, and that other alternatives of implementing the present invention are conceivable.

LIST OF REFERENCE NUMBERS

1. Sampling device
2. Support member
3. Proximal end surface of support member
4. Distal end surface of support member
5. Through passage
6. Inserts
7. Sleeve
8. Protrusion
9. Groove
10. Toothed section
11. Tubular section
12. Distal part of insert
13. Flexible tube
14. Actuation member
15. Shaft
16. Arcuate toothed portion
17. Handle
18. First channel of through passage
19. Second channel of through passage
20. Proximal opening of sleeve
21. Distal end surface of sleeve
22. Orifice of sleeve
23. Through conduit of insert
24. Central cavity of support member
25. Annular rim of actuation member
26. Protrusion on rod
27. Central bore of actuation member
28. Shear pin
29. Nut
30. Collar with asymmetrical teeth
31. Second sealing element
32. First sealing element
33. Rod of support member
34. Linear groove in actuation member
35. Annular groove in actuation member
36. Labelling on handle
37. Distal end surface of insert
38. Eccentric aperture

The invention claimed is:

1. A sampling device for withdrawing a plurality of samples from a fluid container, the sampling device comprising:

a support member for mounting into a port of a fluid container, the support member having a distal end surface facing fluid in the fluid container when mounted into the port and an opposing proximal end surface, wherein the support member comprises a plurality of through passages extending between the distal end surface and the proximal end surface, wherein each through passage comprises a first channel and a second channel within the support member, the first channel extending from the proximal end surface and the second channel extending from the distal end surface and connecting to the first channel, wherein the second channel is arranged eccentrically with respect to the first channel;

a plurality of elongated inserts, each insert comprising a cylindrical distal part rotatably arranged in one of the first channels of the support member and having a distal end surface, and a proximal part protruding beyond the proximal end surface of the support member, wherein each insert comprises a through conduit forming an eccentric aperture within the distal end surface of the cylindrical distal part, the through conduit being alignable and misalignable with the second channel of the respective through passage of the support member by rotating the insert relative to the support member; and an actuation member for sequentially rotating each insert such that by unidirectional movement of the actuation member, each of the inserts is sequentially rotated from a first position of misalignment, through a second position of alignment, to a third position of misalignment of the respective through conduit and the respective second channel.

2. A sampling device according to claim 1, wherein the proximal part of each insert comprises a toothed section, and wherein the actuation member comprises one or more teeth for sequentially engaging with the toothed section of each insert.

3. A sampling device according to claim 1, further comprising a sleeve mounted within each first channel for rotatably receiving the distal part of the respective insert in the sleeve.

4. A sampling device according to claim 3, wherein each sleeve comprises a protrusion on an outer surface thereof, and wherein each first channel comprises a longitudinally extending groove adapted to receive the protrusion of the respective sleeve for preventing rotation of the respective sleeve relative to the support member.

5. A sampling device according to claim 3, wherein the actuation member is rotatable and comprises an arcuate toothed portion for sequentially engaging with the toothed section of each insert such that by unidirectional rotation of the actuation member each of the inserts is sequentially rotated from flail the first position of misalignment, through flail the second position of alignment, to flail the third position of misalignment of the through conduit and the respective second channel.

6. A sampling device according to claim 5, wherein the arcuate toothed portion has an arc length corresponding to an angle of 10-65°.

7. A sampling device according to claim 1, wherein the actuation member comprises a handle for manually rotating the actuation member.

8. A sampling device according to claim 7, wherein the handle comprises labelling on an external surface thereof to indicate a relative rotational position of the actuation member to the alignment of the second channel and the through conduit of each respective insert.

9. A sampling device according to claim 1, wherein the actuation member is only rotatable in one direction.

10. A sampling device according to claim 1, wherein each insert comprises a breakable shear pin to prevent rotation of the insert relative to the support member until the shear pin is broken.

11. A sampling device according to claim 1, wherein the proximal part of each insert is configured to connect to a tube leading to a respective sample receptacle.

12. A sampling device according to claim 1, wherein the sampling device comprises no needles or cannulas.

13. A sampling device according to claim 1, wherein the support member is cylindrical, wherein the distal and proximal end surfaces of the support member form respective circular cylinder surfaces, and wherein the through passages are evenly arranged around a central axis of the cylindrical support member.

14. A sampling device for withdrawing a plurality of samples from a fluid container, the sampling device comprising:

a support member for mounting into a port of a fluid container, the support member having a distal end surface facing fluid in the fluid container when mounted into the port and an opposing proximal end surface, wherein the support member comprises a plurality of through passages extending between the distal end surface and the proximal end surface, wherein each through passage comprises a first channel and a second channel within the support member, the first channel extending from the proximal end surface and the second channel extending from the distal end surface and connecting to the first channel, wherein the second channel is arranged eccentrically with respect to the first channel; and a plurality of elongated inserts, each insert comprising a cylindrical distal part rotatably arranged in one of the first channels of the support member and having a distal end surface, and a proximal part protruding beyond the proximal end surface of the support member, wherein each insert comprises a through conduit forming an eccentric aperture within the distal end surface of the cylindrical distal part, the through conduit being alignable and misalignable with the second channel of the respective through passage of the support member by rotating the insert relative to the support member, wherein each insert comprises a breakable shear pin to prevent rotation of the insert relative to the support member until the shear pin is broken.

15. The sampling device according to claim 14, further comprising an actuation member for sequentially rotating each insert such that by unidirectional movement of the actuation member, each of the inserts is sequentially rotated from a first position of misalignment, through a second position of alignment, to a third position of misalignment of the respective through conduit and the respective second channel, wherein the proximal part of each insert comprises a toothed section, and wherein the actuation member comprises one or more teeth for sequentially engaging with the toothed section of each insert.

16. The sampling device according to claim 14, further comprising a sleeve mounted within each first channel for rotatably receiving the distal part of the respective insert in the sleeve.

17. The sampling device according to claim 16, wherein each sleeve comprises a protrusion on an outer surface thereof, and wherein each first channel comprises a longitudinally extending groove adapted to receive the protrusion of the respective sleeve for preventing rotation of the respective sleeve relative to the support member.

18. The sampling device according to claim 14, further comprising an actuation member for sequentially rotating each insert such that by unidirectional movement of the actuation member, wherein each insert comprises a toothed section, and
wherein the actuation member is rotatable and comprises an arcuate toothed portion for sequentially engaging with the toothed section of each insert such that by unidirectional rotation of the actuation member each of the inserts is sequentially rotated from a first position of misalignment, through a second position of alignment, to a third position of misalignment of the through conduit and the respective second channel.

19. The sampling device according to claim 18, wherein the arcuate toothed portion has an arc length corresponding to an angle of 10-65°.

\* \* \* \* \*